(12) United States Patent
Lemme et al.

(10) Patent No.: US 7,618,807 B2
(45) Date of Patent: Nov. 17, 2009

(54) APPARATUS FOR ELECTROPHORETIC IN SITU TISSUE STAINING

(75) Inventors: Charles Lemme, Tucson, AZ (US); William Richards, Tucson, AZ (US); David Bryant, Raleigh, NC (US); Catherine Wolf, Eckbolsheim (FR); Andrew Ghusson, Tucson, AZ (US); Austin Ashby, Tucson, AZ (US); Wayne Showalter, Tucson, AZ (US); Anthony Hartman, Tucson, AZ (US); Brian Kram, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 265 days.

(21) Appl. No.: 11/863,834

(22) Filed: Sep. 28, 2007

(65) Prior Publication Data
US 2008/0020450 A1    Jan. 24, 2008

Related U.S. Application Data

(62) Division of application No. 10/848,775, filed on May 18, 2004, now abandoned.

(60) Provisional application No. 60/471,810, filed on May 19, 2003.

(51) Int. Cl.
*C12M 1/42* (2006.01)
*C12M 3/00* (2006.01)

(52) U.S. Cl. .................. 435/285.2; 435/283.1

(58) Field of Classification Search ............ 435/283.1, 435/285.1–285.3
See application file for complete search history.

(56) References Cited

U.S. PATENT DOCUMENTS

| 2,992,979 | A | 7/1961 | Magnuson et al |
| 3,384,564 | A | 5/1968 | Ornstein et at |
| 3,494,846 | A | 2/1970 | Arquembourg |
| 3,677,930 | A | 7/1972 | Meshbane et at |
| 3,844,926 | A | 10/1974 | Smyth et at |

(Continued)

FOREIGN PATENT DOCUMENTS

| WO | WO95/11988 | 5/1995 |
| WO | WO99/04850 | 2/1999 |

*Primary Examiner*—Walter D Griffin
*Assistant Examiner*—Shanta G Doe
(74) *Attorney, Agent, or Firm*—Ventana Medical Systems, Inc.

(57) ABSTRACT

The present invention introduces a radically different way of accelerating biomolecule conjugates into tissue, and hence towards their targets for purposes of tissue staining. The invention provides for an order of magnitude improvement over the prior art diffusion process used to stain tissue. The invention comprises a method of tissue staining by applying an electric field to a tissue sample in the presence of an electrolyte and biomolecular conjugates of interest suspended in the electrolyte. Typical staining times are reduced to seconds as opposed to 30-120 minutes common in the prior art. The invention is also directed to devices for performing the method.

17 Claims, 10 Drawing Sheets

U.S. PATENT DOCUMENTS

| | | | | |
|---|---|---|---|---|
| 4,476,004 A | * | 10/1984 | Pohl | 435/285.2 |
| 4,561,961 A | * | 12/1985 | Hofmann | 204/643 |
| 5,134,070 A | * | 7/1992 | Casnig | 435/173.6 |
| 5,355,439 A | | 10/1994 | Bernstein et al. | |
| 5,382,552 A | | 1/1995 | Shah et al. | |
| 5,536,382 A | | 7/1996 | Sunzeri | |
| 5,595,707 A | | 1/1997 | Copeland et al. | |
| 5,654,199 A | | 8/1997 | Copeland et al. | |
| 5,737,499 A | | 4/1998 | Bernstein et al. | |
| 5,830,877 A | | 11/1998 | Carson et al. | |
| 6,093,574 A | | 7/2000 | Druyor-Sanchez et al. | |
| 6,296,809 B1 | | 10/2001 | Richards et al. | |
| 6,409,774 B1 | | 6/2002 | Kerschmann et al. | |
| 2003/0119028 A1 | | 6/2003 | Graves et al. | |

* cited by examiner

APPARATUS FOR ELECTROPHORETIC IN SITU TISSUE STAINING

RELATED APPLICATIONS

This is a divisional of U.S. patent application Ser. No. 10/848,775, filed May 18, 2004 now abandoned, and claims the benefit of U.S. Provisional Patent Application No. 60/471,810, filed May 19, 2003. Both of these related applications are incorporated by reference herein.

BACKGROUND

1. Field of the Invention

This invention relates generally to the field of automated tissue staining apparatus, and in particular is a new method of introducing stains into tissue using electrophoresis.

2. Description of Related Art

Tissue staining is an ancient art by modern standards that goes back over one hundred years. Recently, efforts have been made to automate the procedure of applying different types of chemical and biochemical stains to tissue sections. Instruments that have been invented for this purpose include the Ventana Medical Systems' line of dual carousel-based instruments such as the 320, ES®, NexES®, BENCHMARK®, and the BENCHMARK® XT. Patents that describe these systems include U.S. Pat. Nos. 5,595,707, 5,654,199, 6,093,574, and 6,296,809, all of which are incorporated herein by reference in their entirety. Another type of automated stainer is the TechMate® line of stainers, described in U.S. Pat. Nos. 5,355,439 and 5,737,499, both of which are incorporated herein by reference in their entireties.

The rate of Immunohistochemical and in situ hybridization staining of microtome-sectioned tissue on a glass slide is limited by the speed at which the biomolecules of interest can diffuse into the tissue from an aqueous solution placed in contact with the tissue section. Intact tissue presents many barriers to diffusion such as the lipid bilayer membranes that enclose individual cells and organelles, and the effects of cross-linking that the fixation process generates. The protein antibody or DNA probe molecules of interest are relatively large, ranging in size from a few kilo Daltons to several hundred kilo Daltons, which causes them to diffuse slowly into solid tissue with typical times for sufficient diffusion being in the range of several minutes to a few hours. A typical incubation period is thirty minutes at 37 degrees centigrade.

The diffusion rate is driven by concentration gradient so the rate can be increased by increasing the concentration of the conjugate in the reagent. However, this has two detrimental effects. First, the conjugates are often very expensive, so increasing their concentration is wasteful and not economically viable. Second, the excessive amount of conjugate that is driven into the tissue, when high concentrations are used, gets trapped in the tissue, and cannot be rinsed out and causes high levels of background staining. This background staining is called non-specific staining and, in an informational sense, is just noise. In order to reduce the noise and increase the signal of specific staining, low concentrations of conjugate are used with long incubation times to allow the conjugate to find and bind to only the specific sites.

Electrophoresis is an electrochemical separation technology commonly applied to separate biological molecules on the basis of their charge-to-mass ratio. Generally, a gel slab is prepared from a suitable polymeric material such as polyacrylamide by adding water to it in sufficient amount to create a semi-solid gelatinous slab. This is the matrix used to both contain the sample to be separated, and transmit the electric current used to electromotively move the various charged molecules. The pH of the gel can be manipulated to charge a biomolecule that is otherwise uncharged, thereby giving it the prerequisite net charge so that it will move when a field is applied to it. When the gel has an electric field applied to it, the charged molecules will migrate through the gel towards their opposite pole, i.e., negatively charged biomolecules will move towards the positive pole, and vice versa. The process is very commonly used in the biological research field to separate complex mixtures, and is termed "PAGE" (Polyacrylamide gel electrophoresis). A related technology is capillary electrophoresis ("CE"), which is the same basic electrochemical separation performed in thin glass capillary lumens filled with an electrolytic solution.

There continues to be a need for faster introduction of biomolecules into tissue sections, and for lower amounts of non-specific background staining.

SUMMARY OF THE INVENTION

The present invention introduces a radically different way of accelerating biomolecule conjugates into tissue for purposes of tissue staining, and hence towards their targets. The invention provides for an order of magnitude improvement over the prior art diffusion process used to stain tissue. The invention comprises a method of tissue staining by applying an electric field to a tissue sample in the presence of an electrolyte and a biomolecular conjugate molecule of interest suspended in the electrolyte. Typical staining times are reduced to seconds as opposed to 30-120 minutes common in the prior art.

It is an object of this invention to accelerate the movement of conjugate molecules from the aqueous solution into the solid tissue. Another object is to reduce the background staining due to conjugates that are not bound to specific sites. A further object is to reduce the concentration of the conjugate required in the reagent.

DESCRIPTION OF THE PREFERRED EMBODIMENTS

Figure 1:
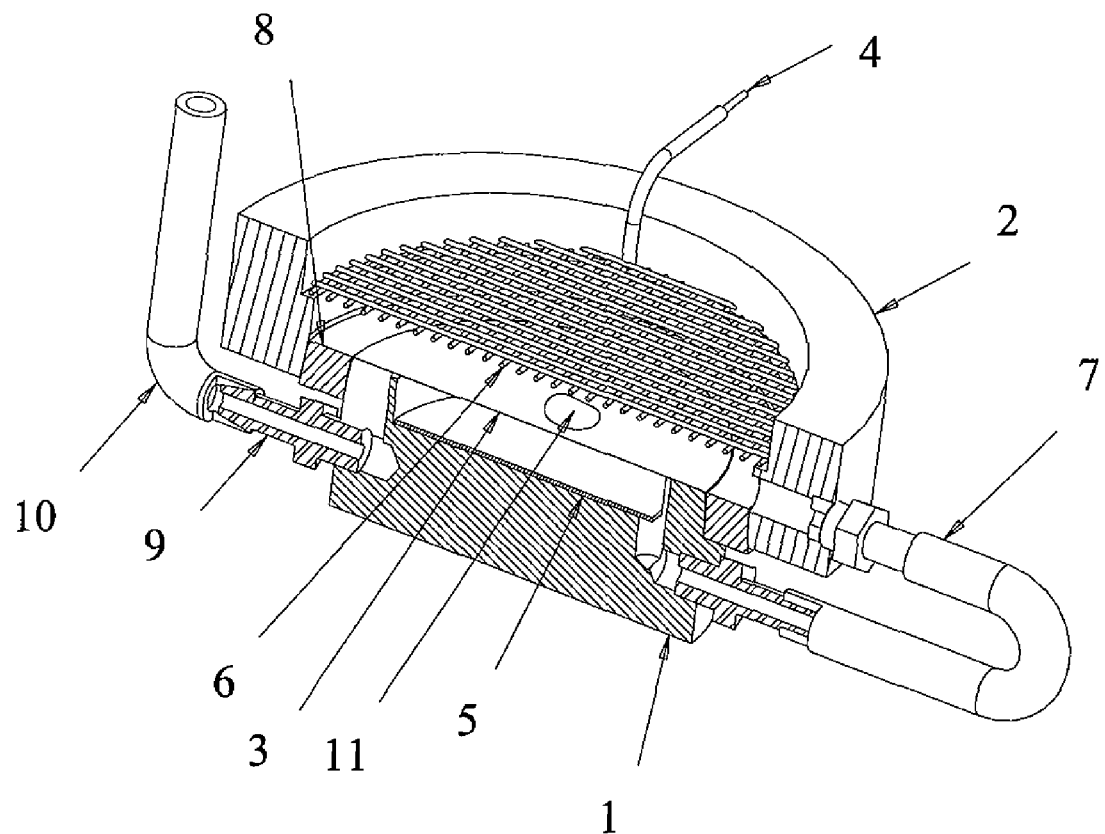
FIG. 1 shows a cross-sectional view of an apparatus using this method. It uses electrophoresis to cause molecules to pass into and through a thin cut piece of tissue.

The invention is directed to a method of introducing a conjugate molecule into tissue comprising applying an electric field to the tissue in the presence of an electrolyte and a conjugate molecule of interest suspended in the electrolyte. A conjugate molecule may be any molecule that has a complementary binding portion that, when brought into proximity to its complementary binding site, binds to the site. Antibodies having complementarity determining regions, and DNA oligomers that have matching sequences to their target DNA, are two examples of conjugate molecules. The conjugate molecules of interest are all charged when dissolved in an aqueous solution of electrolyte of the correct pH. The net charge facilitates their movement through the electrolyte solution by the electric field. Tissue includes both tissue sections and intact cells prepared according to conventional methods such as cytospins or Thin Preps.

The technology generally known as Electrophoresis has been used for many years, both in research and industry to separate molecules of differing sizes and charges. Descriptions for the use of electrophoresis are given in U.S. Pat. Nos. 2,992,979; 3,384,564; 3,494,846; 3,677,930; 3,844,926; 5,382,522 and 5,536,382 among others. The prior art describes applying the electric field across a liquid or gelatinous material, such as agrose, while the solution containing the molecules of interest is placed at one end. The molecules of interest migrate through the material, at rates that depend on their net charge and molecular weights. Some of the prior art discloses the use of electrophoresis to separate human biomolecules for clinical applications. In U.S. Pat. No. 5,536,382, methods are provided for the analysis of constituents of human biological fluids using capillary electrophoresis. A clinical sample was mixed with a labeled reagent which specifically binds the analyte of interest. Capillary electrophoresis is then used to resolve bound from unbound reagent, and the constituents quantitated by measuring directly or indirectly the amount of bound reagent. In U.S. Pat. No. 5,382,522, a serum or plasma sample was assayed to determine the concentration of two different analytes selected from the group consisting of creatine kinase-MB species and creatine kinase-BB species. However, none of the prior art uses an electric field to move molecules into human tissue.

The most general description of this invention is that it is any method that applies an electric field across both an aqueous solution containing conjugate molecules and some tissue of interest in order to use the electrophoretic forces to drive the conjugate molecules into the tissue. In the preferred embodiment, the tissue is human tissue that is suspected of harboring some disease and has been cut on a microtome to a thin section. However, cell preparations comprising intact cells adhered to a flat surface for further processing are also encompassed by this general method. A thin section is generally between two and thirty microns thick. There are several different ways to apply the electric field to thin cut tissue, three of which are described below.

A first preferred method is to mount the thin cut tissue on a porous membrane, apply a conductive aqueous fluid to both sides, add reagent containing the conjugate into the fluid on at least one side, place electrodes on opposite sides and apply an electric field between the electrodes. Direct current is the preferred mode of generating the electric field, but alternating current may also be used. FIG. 1 shows a cross sectional view of an apparatus using this method. It uses electrophoresis to cause molecules to pass into and through a thin cut piece of tissue.

The tissue 11 is attached to a porous membrane 3. The tissue can be from any area of the body, but tests have been run using tonsil. The membrane can be made from any hydrophilic, porous material. One method that has been tried is to use PTFE film, commonly called "plumber's tape". The PTFE film must me made hydrophilic by polymerizing polyvinyl alcohol to its surface before the tissue will bond to it. The lower electrode 5 is made from a solid disk of metal, preferably 316 SS and is placed into the bottom of the five millimeter deep depression in the lower ring, 1. This depression forms a basin below the membrane 3. An electrical lead, not shown, is attached to the lower electrode and passes out through the lower ring through a sealed hole, not shown, and is connected to one leg of the electrophoresis power supply, not shown. The membrane is stretched over the top of the lower ring, and down over its outer, tapered diameter. The membrane is retained by pressing the intermediate ring 8 over the lower ring 1 trapping the membrane 3 between the two tapered diametrical surfaces. The upper ring 2 is pressed onto the intermediate ring 8 forming another five millimeter deep basin, this one being above the membrane 3. This upper basin is hydraulically connected to the lower basin by means of two fittings 9 and a section of tubing 7. The fittings 9 are standard barb fittings made of thermoplastic and the tubing 7 is standard Tygon. The upper electrode, 6, is made of stainless steel wire mesh which allows reagent to be poured into the upper basin and keeps the top surface of membrane, 3, and the tissue, 11, visible. Upper electrode, 6, is connected to the electrophoresis power supply, not shown, by means of wire, 4. Another section of Tygon tubing, 10, is connected to a third barbed fitting, 9, which bleeds air out of the lower basin as fluid is poured into the upper basin. In operation, the upper basin is filled with conductive reagent, such as Tris-Acetate EDTA buffer at 10% concentration. This reagent also flows into the lower basin, displacing the air through the passages leading to tubing, 10. After the basins are filled, a conjugate is placed into the upper basin. Tests have been run using anti-CD34 antibody which attaches to capillary tissue in the tonsil tissue. The anti-CD34 is first mixed 1:1 with glycerol so that is sinks through the Tris buffer to the top of the tissue and the membrane. An electric potential of ten volts is applied across the ten millimeters of distance between the electrodes, providing an electric field with a strength of 100 volts per meter. The anti-CD34 antibody moves through the five micron thick tissue in less than ten seconds. The apparatus is disassembled, and the area of the tissue is cut out of the membrane. It is then processed with a standard chromagin detection kit. The capillaries in the tissue stand out against the background.

If a membrane is used to support the tissue during electrophoresis, the membrane containing the tissue must be removed from its support structure, applied to a glass slide and coverslipped. In the preferred embodiment, the membrane must be transparent after it is coverslipped. In order for the membrane to be transparent after coverslipping, it must have an index of refraction that is very near that of the coverslip media. Standard, xylene soluble coverslip media, such as Super-Mount™, has an index of refraction of 1.54 which is very close to that of typical proteins in human tissue. Membranes that have an index of refraction close to this are PET and nylon 6.

A second preferred method is to apply an electric field across the aqueous solution and the thin cut tissue of interest is to coat the glass slide with a conductive layer, apply the tissue directly to the top of the conductive layer, add a conductive reagent of the correct pH that contains the conjugate molecules of interest over the top of the tissue, cover the conductive reagent with a second electrode and then apply a potential between the conductive layer on the slide and the upper conductive electrode. After the conjugate has been driven into the tissue and sufficient time has elapsed for the conjugates to find their specific sites (a few seconds at most), the electric potential can be reversed, so that any unbound conjugates are driven out, reducing the background noise of non-specific binding.

The conductive layer needs to be transparent so that after the staining is complete, a pathologist can look at the tissue through a microscope with the tissue illuminated from below. Two possible candidates for a conductive, transparent film are gold and ITO (Indium Tin Oxide). Both are applied as very thin layers in a vacuum chamber. Any material that is both transparent, conductive and resistant to oxidation can be used.

Figure 2:
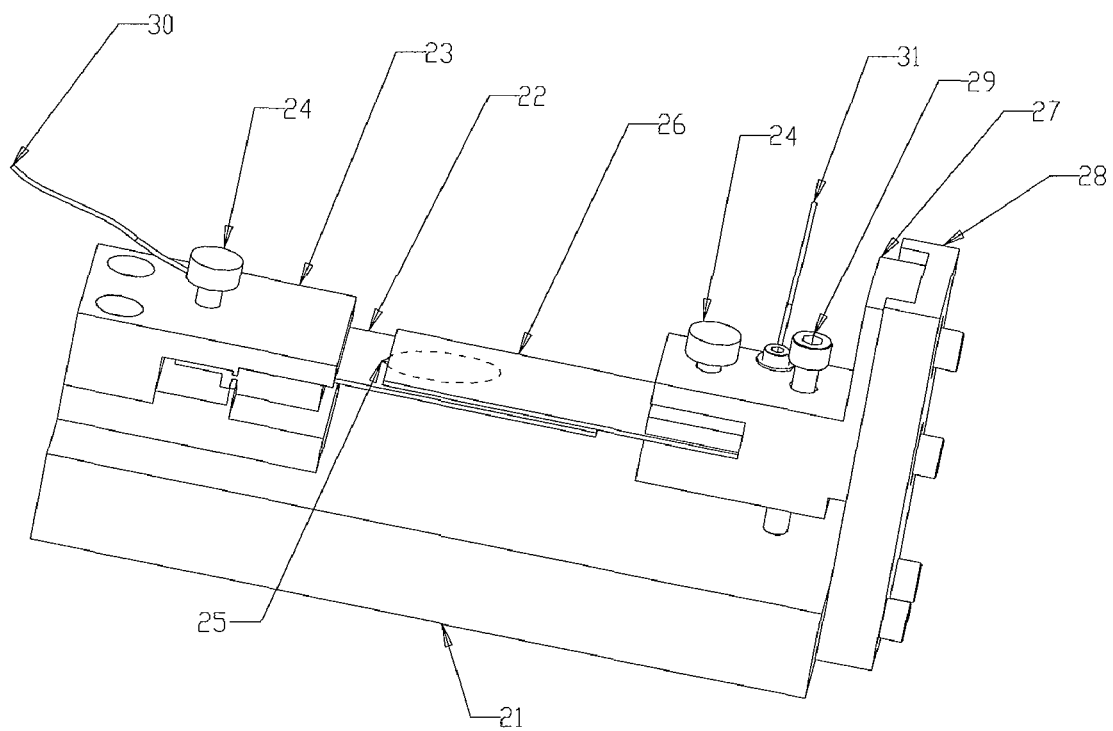
FIG. 2 shows an ITO coated slide with a capillary gap.

FIG. 2 shows an apparatus for applying an electrical field across a capillary gap of reagent that contains conjugate molecules and across a thin cut layer of tissue that is adhered to an ITO coated glass slide 22. All the components are attached to a non-conductive base plate, 21, made from Ultem® 1000. The microscope slide, 22, is retained in the fixed clamping fixture, 23, by the force exerted by thumb screw, 24. All of the clamping fixture, 23, is made of conductive material, such as stainless steel. The tissue, 25, is adhered to the top of the ITO surface of slide 22. The upper electrode, 26, is clamped into sliding clamping fixture, 27, which is also made of stainless steel and slides in a groove in backing plate 28. The size of the capillary gap between the slide 22 and the upper electrode 26 is adjusted by screw 29 which is threaded into sliding clamp 27 and pushes against the top surface of base 21. The wire leads, 30, 31 are connected to the electrophoresis power supply (not shown).

The resistance of an ITO coated surface is about 15 ohms per square inch. The slides are 25 mm wide and have 50 mm of length extending from the fixed clamp, 2. This means that the resistance of the film along the length of the 50 mm of extended slide is 30 ohms. The resistance of the capillary gap is much less, being about 0.33 ohm for a 200 µm thick gap of reagent. In order for the electric field across the gap to be constant, the linear resistance of the upper electrode must match that of the ITO coating. This can be done by using another ITO coated slide as the top electrode or by using a platinum or gold coated slide that has the same resistance as the slide coating. The potential that needs to be applied depends on the resistance of the coatings and fluid, the length of overlap and the resistance of the capillary gap. The electrical potential is applied to the capillary gap by connecting the wires to a power supply. In order to produce a uniform electric field of one volt per millimeter over a 200 µm gap (0.20 volt), a potential of 24 volts is required across the electrodes.

Figure 3:
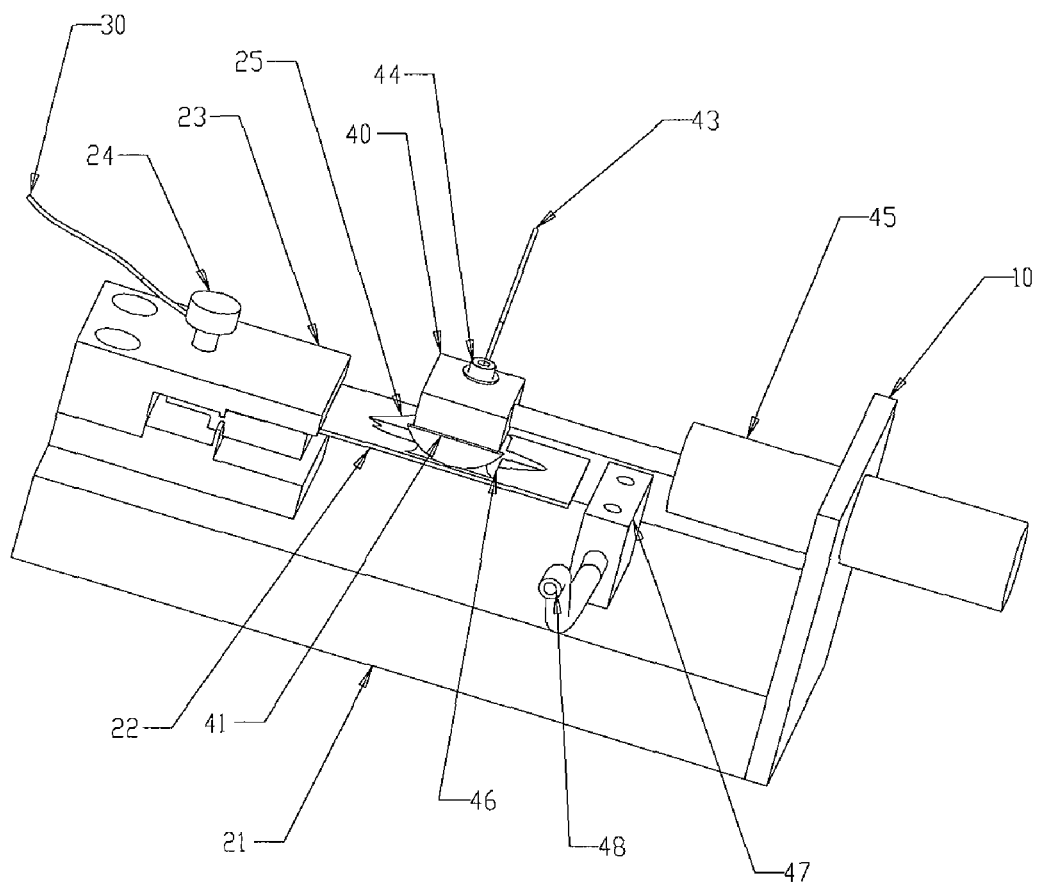
FIG. 3 is an ITO coated slide with a moving upper electrode shown over the slide.
Figure 4:
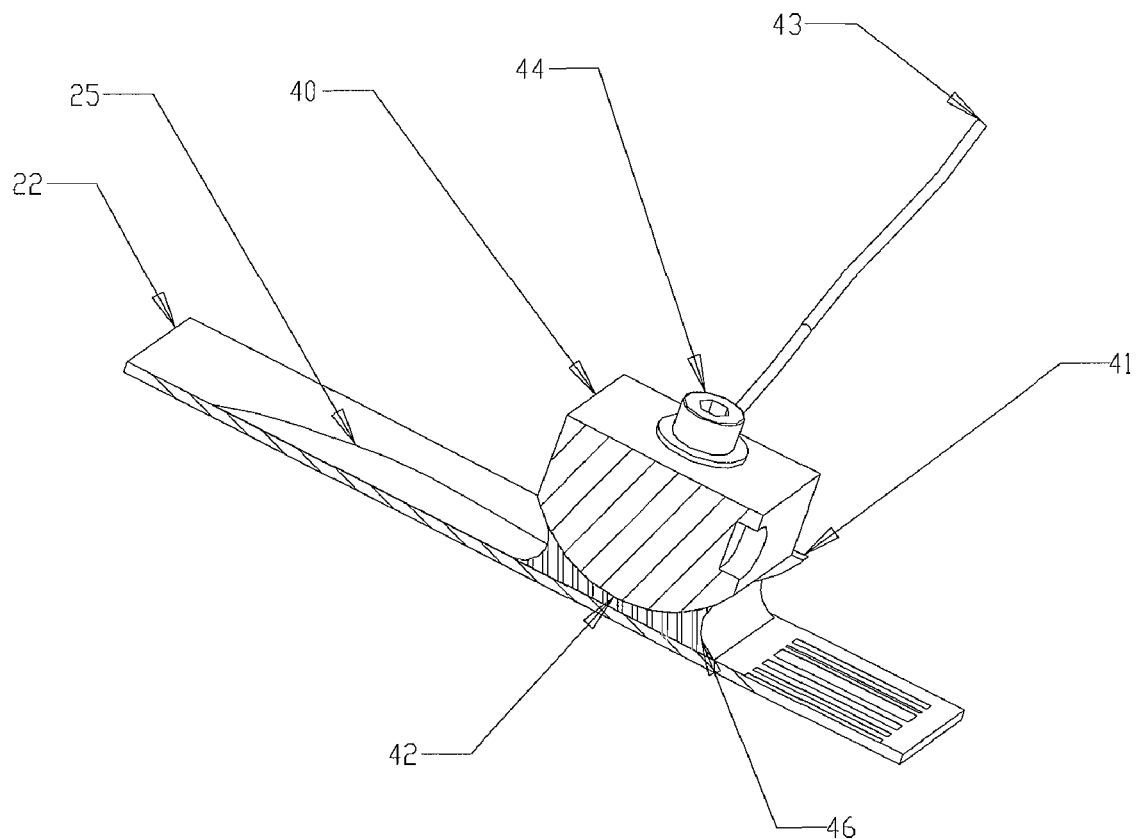
FIG. 4 is a cross-section through the movable upper electrode.

A third preferred method of applying the required potential across the reagent and tissue is to use a curved, movable upper electrode, as shown in FIGS. 3 and 4 in conjunction with an ITO coated microscope slide 22. The slide 22 is clamped in the fixed clamp 23 as in the previous embodiment. However, instead of a fixed upper electrode 26 the moving upper electrode 40, is attached to an air cylinder 45 that moves it lengthwise along the slide. The moving upper electrode 40 is 25 mm wide and has a curved lower surface that is stepped. The outer rims 41 of the movable electrode 40 are one millimeter wide at both sides and extend radially 200 µm beyond the curved lower surface 42 (see FIG. 4) which lies between the two rims 41.

The two rims 41 slide on the surface of the slide while the raised surface 42 is approximately 200 µm above the slide. The movable electrode 40 is made of a non-conductor such as Ultem® 1000. Its curved lower surface 42 lies between the rims 41 and is plated with platinum and is electrically connected to the lead wire 43 which in turn is secured to the Ultem electrode 40 by means of screw 44. Tissue 25 is adhered to the ITO surface of slide 22 and a small volume of about 15 µl of the reagent that contains the conjugates of interest is placed on the slide from a pipette (not shown). The air cylinder 45 pushes the movable electrode 40 onto the slide where it contacts the 15 µl puddle of reagent. The reagent is attracted to the lower platinum-plated surface 42 of the moveable electrode 40 forming a meniscus 46. The surface tension of the reagent strongly attracts the reagent to the platinum-plated surface 42 and the top of the slide 22, and retains it there while the electrode 40 is moved axially along the slide 22 by the air cylinder 45. The reagent wets the top surface of the slide and the tissue as it slides across them and the electric potential provides the electrophoretic force that drives the molecules into the tissue. The reagent is strongly mixed by the shear forces in the reagent as the electrode moves. With this apparatus, the potential can be reversed to drive out conjugate that is not bound to specific sites.

Even though the resistance of the ITO on the slide between the electrode and the clamped end of the slide varies significantly, a constant potential is maintained between the platinum coated surface and the ITO surface of the slide by means of a constant current circuit that supplies power to the two wires. A constant current circuit is a well-known device to those skilled in the art of transistor circuitry.

The reagents used in any step need to be removed before reagents for the next step are applied. This is accomplished in this embodiment by bringing the movable electrode 40 off of the slide 22 and onto rinse block 47. Rinse block 47 has holes in its upper surface that are fed by tubing 48. Rinse fluid to the rinse block 47 is controlled by a valve, not shown. Electrode 40 is rinsed at the rinse block 47 then, while it is covered with rinse solution, it is returned to the slide 22. On the slide it picks up more reagent, and is again returned to the rinse block 47. By a series of these motions, the reagent on the slide is serially diluted until it is sufficiently dilute as not to cause any interference with the next reagent.

Figure 5:
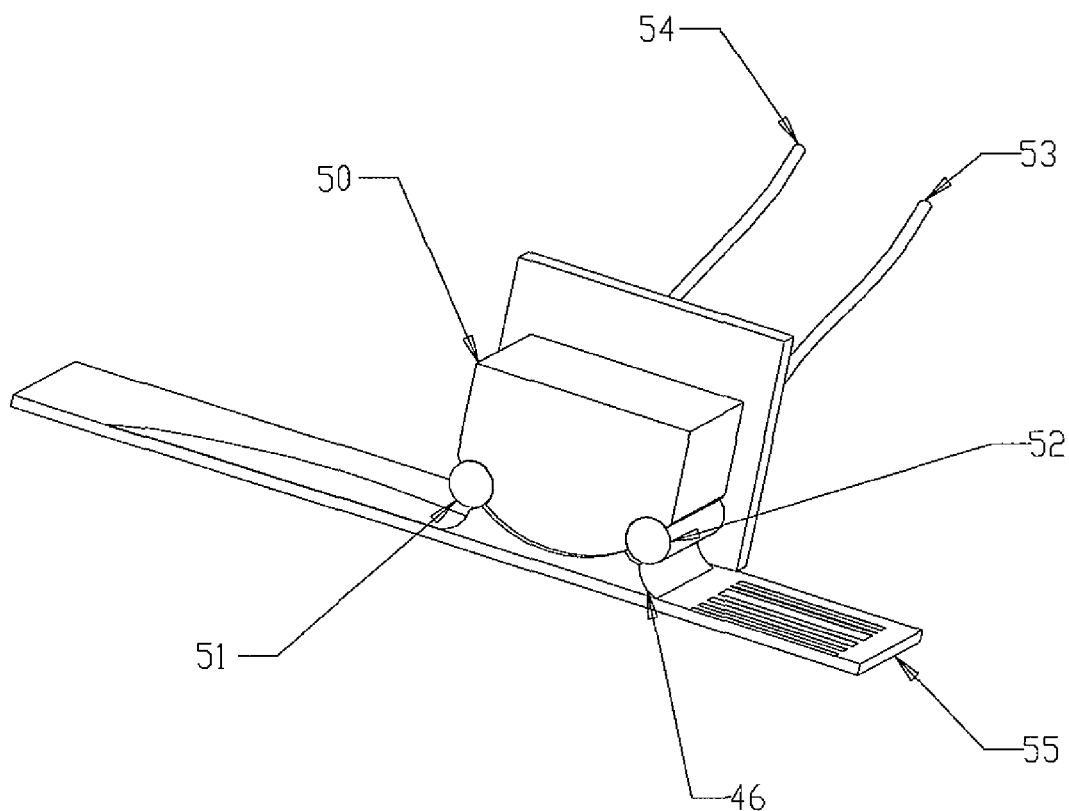
FIG. 5 is another cross-section through the movable dual electrode of embodiment four having incorporated conductive rods.

A fourth preferred method (shown in FIG. 5) of applying a potential across the tissue is similar to method three but does not use a conductive coating on the slide. Instead of a conductive lower surface on the insulated movable block, two conductive rods, 51, 52, were used. The rods are located on opposite ends of the movable block 50 with their axes running across the narrow width of the slide. The voltage is applied between the two rods, one rod connected to the positive potential lead, 53 and the other connected to the negative potential lead 54. As current flows from one rod to the other through the reagent on the slide 55, the charged molecules are driven into the tissue. As in method three, the block was moved up and down the length of the slide while the current was being applied. Rinsing of the slide may be accomplished in the same manner as described above for method three.

Experiment 1. Electrophoretic tissue staining using anti-CD34 antibody in tonsil.

The following experiment was run to determine if antibody could be introduced electrophoretically into tissue. The tissue was adhered to a hydrophilic polytetrafluoroethylene (PTFE) membrane (TEFLON® Plumber's Tape) to enable manipulation and orientation of the tissue in the gel, and then embedded in an agarose gel for subsequent electrophoresis.

Procedure: four sections of 5 µm-thick human tonsil were mounted to PVA-treated hydrophilic PTFE membrane, air dried for 48 hours, overnight dried at 60° C., manually de-paraffinized and re-hydrated (standard process of dipping sections sequentially in xylene, then 100% EtOH, 90% EtOH, 80% EtOH, 70% EtOH, and finally 100% H2O). The PTFE membrane was made hydrophilic by wetting in Isopropyl alcohol first, then soaking for several hours in a solution of 0.1% polyvinyl alcohol in phosphate buffer, pH 2.2 and 5% glutaraldehyde, and rinsed in DI water. Any hydrophilic membrane that will pass antibodies will work, however.

Figure 6:
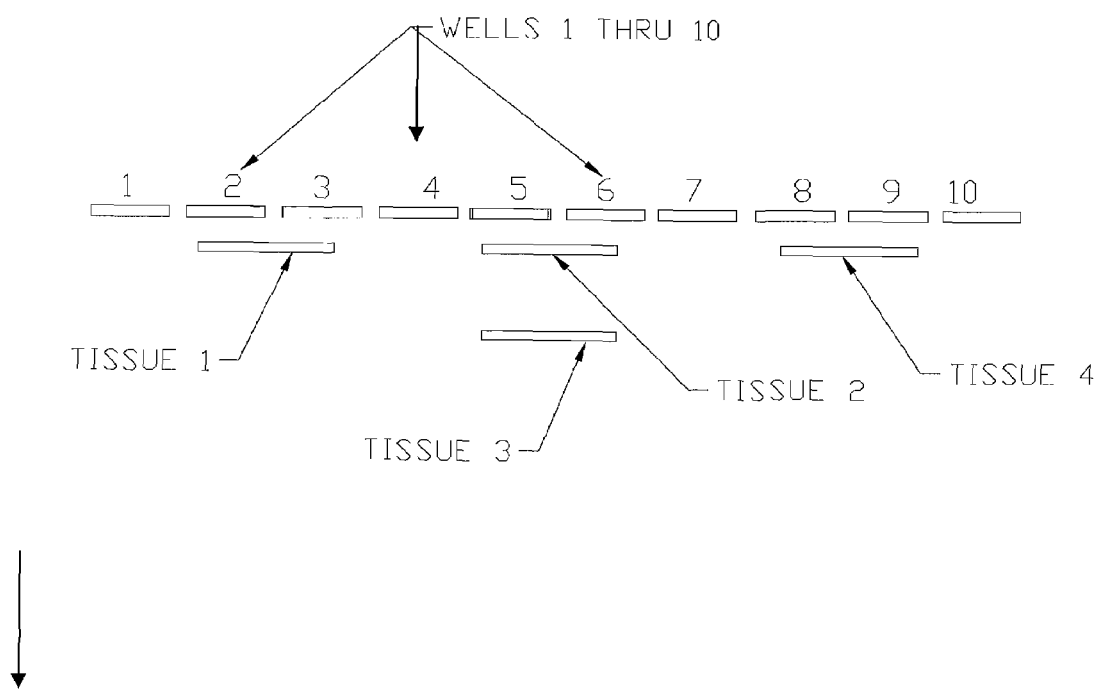
FIG. 6 is a schematic of wells and tissue positions in an agarose gel.

With regard to FIG. 6, ten wells are shown, numbered 1-10. Three of the tissue/membrane sections, shown as Tissues 2-4, were mounted in 1% agarose (GibcoBRL, Cat. No. 15510-

019 in 1×TAE buffer, Sigma Cat. No. T9650) and cut out. Tissue 1 was not mounted in agarose prior to pouring the gel and was positioned in the electrophoresis apparatus (Owl Model B1A, flatbed) adjacent to wells 2 and 3. Tissues 2-4 were first embedded in agarose than positioned vertically as shown in FIG. 6. The vertical positioning places the tissue sections in the direct path of the antibodies from the wells so that the antibodies must migrate through the tissue under the urging of the electric field and in the direction of the large arrow at the left of FIG. 6. The apparatus was filled with 1% agarose and allowed to solidify. 25 µl of anti-CD34 antibody (Ventana Medical Systems, Tucson, Ariz., Cat. No. 790-2927) was diluted 50% with glycerol (Sigma Cat No. G6279) and bromo phynol blue (Sigma Cat. No. B3269) and was added to wells 2, 3, 5, 6, 8 and 9. The electrophoresis apparatus was run at 45V for 90 minutes. An additional 25 µl of anti-CD34 was added to wells 2 and 9 to see if additional antibody lead to increased staining, and 25 µl of FITC-labeled human IgG was added to wells 1 and 10 to insure that under these test conditions the antibody was migrating in the proper direction. The apparatus was run for an additional 120 minutes at 45V. The tissues on the membranes were removed from the agarose by peeling the agarose away and a streptavidin/DAB detection kit applied manually (Ventana Medical Systems, Tucson, Ariz., Cat. No. 760-124).

Figure 7:
FIG. 7 is a photomicrograph of Tissue Section 1.
Figure 8:
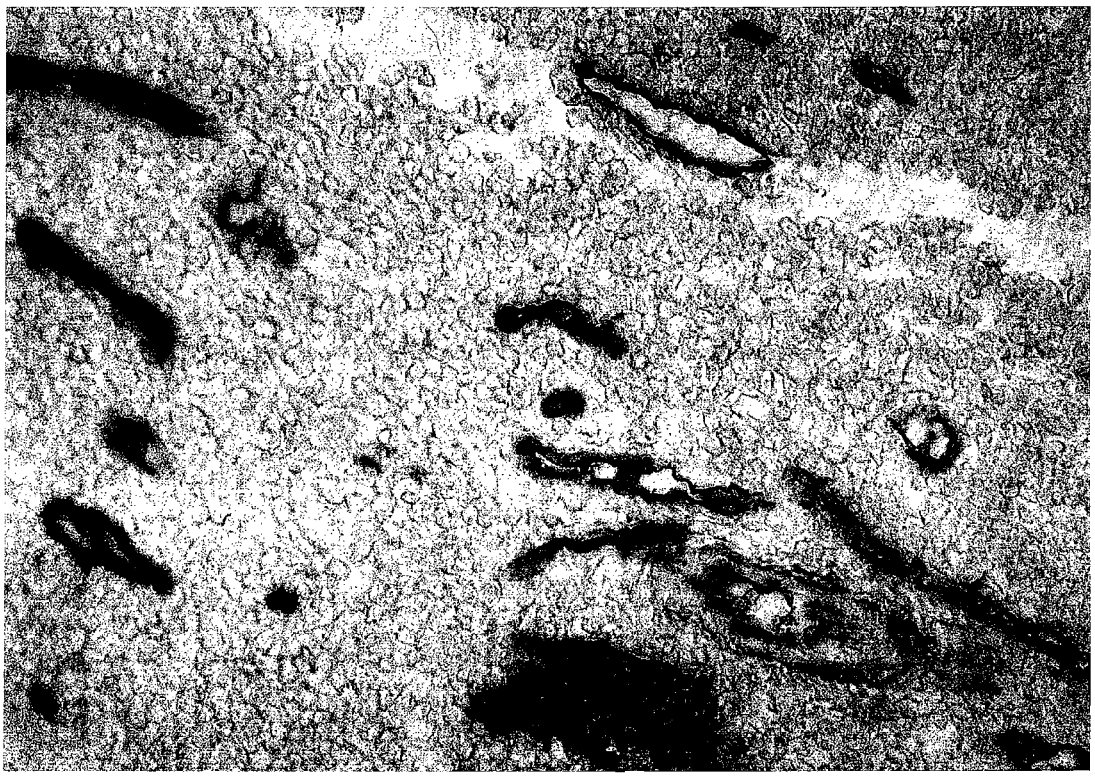
FIG. 8 is a photomicrograph of Tissue Section 2.
Figure 9:
FIG. 9 is a photomicrograph of Tissue Section 3.
Figure 10:
FIG. 10 is a photomicrograph of Tissue Section 4.

Results: Photomicrographs of the stained tissue sections corresponding to antibody from wells 2-3, 5-6, and 8-9 are shown in FIGS. 7-10. FIG. 7 shows Tissue Section 1, which was in front of wells 2-3. FIG. 8 shows Tissue Section 2, which was directly in front of wells 5-6. FIG. 9 shows Tissue Section 3, which was in front of Tissue Section 2. FIG. 10 shows Tissue Section 4, which was in front of wells 8-9. Tissue sections 1 (FIG. 7) and 4 (FIG. 10) were stained equally and darker than Sections 2 and 3. Section 3 was stained significantly lighter than section 2.

CONCLUSIONS

1. Electrophoresis is able to drive anti-CD34 antibody into tonsil tissue and through tonsil tissue that is mounted on PTFE membrane.
2. The antibody binds to its antigen under these conditions.
3. The more antibody that is passed through the tissue, the darker the stain.
4. Background coloration is acceptable.

Although certain presently preferred embodiments of the invention have been described herein, it will be apparent to those skilled in the art to which the invention pertains that variations and modifications of the described embodiments may be made without departing from the spirit and scope of the invention. For instance, although direct current is normally used for electrophoresis, it is contemplated that alternating current could be used also. Accordingly, it is intended that the invention be limited only to the extent required by the appended claims and the applicable rules of law.

We claim:

1. A device for electrophoretically directing conjugate molecules into a tissue sample, comprising:
   a microscope slide, the microscope slide having a transparent conductive surface onto which the tissue sample is adhered;
   an electrically conductive clamping fixture that retains the microscope slide and makes electrical contact with the transparent conductive surface;
   a curved electrode positioned adjacent to the transparent conductive surface; and
   a source of electrical potential between the clamping fixture and the curved electrode.

2. The device of claim 1, wherein the curved electrode is mounted on a curved lower surface of a non-conductive block, the non-conductive block further comprising two rims that hold the curved electrode in a spaced relationship with the transparent conductive surface.

3. The device of claim 2, wherein the non-conductive block is movable and the non-conductive block slides on the rims across the transparent conductive surface.

4. The device of claim 3, wherein the movable block is attached to an air cylinder that moves the non-conductive block across the transparent conductive surface on the rims.

5. The device of claim 1, wherein the transparent conductive surface comprises indium tin oxide or gold.

6. The device of claim 1, wherein the source of electrical potential comprises a constant current circuit.

7. The device of claim 3, further comprising a rinse block for rinsing the electrode.

8. The device of claim 3, wherein the movable block is configured to move lengthwise along the microscope slide.

9. A device for electrophoretically directing conjugate molecules into a tissue sample, comprising:
   a microscope slide onto which the tissue sample is adhered;
   a movable electrically-insulated block, the block having at least two electrodes of opposite polarity positioned on it, the block held in a spaced-apart relationship with the microscope slide by two rims on the block; and
   a source of electrical potential between the at least two electrodes.

10. The device of claim 9, wherein the movable block has a curved lower surface.

11. The device of claim 9, wherein the movable block is attached to an air cylinder that moves the block.

12. The device of claim 9, wherein the source of electrical potential comprises a constant current circuit.

13. The device of claim 9, further comprising a rinse block for rinsing the electrode.

14. The device of claim 9, wherein the movable block is configured to move lengthwise along the microscope slide.

15. The device of claim 9, wherein the at least two electrodes are located on opposite ends of the block.

16. The device of claim 9, wherein the at least two electrodes comprise conductive rods.

17. The device of claim 14, wherein the at least two electrodes comprise conductive rods that are mounted on the block with their axes running across the narrow width of the microscope slide.

* * * * *